(12) United States Patent  
Manwaring et al.

(10) Patent No.: US 9,044,195 B2  
(45) Date of Patent: Jun. 2, 2015

(54) IMPLANTABLE SONIC WINDOWS

(71) Applicants: Jotham Charles Manwaring, Tampa, FL (US); Kim Herbert Manwaring, Phoenix, AZ (US)

(72) Inventors: Jotham Charles Manwaring, Tampa, FL (US); Kim Herbert Manwaring, Phoenix, AZ (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/268,574

(22) Filed: May 2, 2014

(65) Prior Publication Data

US 2014/0330123 A1 Nov. 6, 2014

Related U.S. Application Data

(60) Provisional application No. 61/818,724, filed on May 2, 2013.

(51) Int. Cl.
| | | |
|---|---|---|
| *A61N 7/00* | (2006.01) | |
| *A61B 8/08* | (2006.01) | |
| *A61N 7/02* | (2006.01) | |
| *A61B 17/00* | (2006.01) | |
| *A61B 19/00* | (2006.01) | |

(52) U.S. Cl.
CPC ............ *A61B 8/5223* (2013.01); *A61B 8/0808* (2013.01); *A61N 7/02* (2013.01); *A61B 2017/00924* (2013.01); *A61B 2019/5276* (2013.01); *A61N 2007/003* (2013.01)

(58) Field of Classification Search
CPC ............ A61B 2017/00924; A61B 2019/5276; A61B 8/0808; A61B 8/5223; A61N 2007/003; A61N 7/02

USPC .................... 600/437, 438; 601/2, 3; 606/280
See application file for complete search history.

(56) References Cited

U.S. PATENT DOCUMENTS

| | | |
|---|---|---|
| 2,671,444 A | 3/1954 | Pease, Jr. |
| 3,048,537 A | 8/1962 | Pall et al. |
| 3,178,728 A | 4/1965 | Christensen |
| 3,579,643 A | 5/1971 | Morgan |
| 4,089,071 A | 5/1978 | Kalnberz et al. |
| 4,164,794 A | 8/1979 | Spector et al. |
| 4,479,271 A | 10/1984 | Bolesky et al. |
| 4,502,161 A | 3/1985 | Wall |
| 4,531,916 A | 7/1985 | Scantlebury et al. |
| 4,535,485 A | 8/1985 | Ashman et al. |
| 4,542,539 A | 9/1985 | Rowe, Jr. et al. |
| 4,550,448 A | 11/1985 | Kenna |
| 4,636,215 A | 1/1987 | Schwartz |
| 4,693,721 A | 9/1987 | Ducheyne |
| 4,756,862 A | 7/1988 | Spector et al. |
| 4,778,472 A | 10/1988 | Homsy et al. |
| 4,790,849 A | 12/1988 | Terino |
| 4,863,474 A | 9/1989 | Brown et al. |

(Continued)

OTHER PUBLICATIONS

Holtmaat, et al. "Long-term, high-resolution imaging in the mouse neocortex through a chronic cranial window", 2009 Nature Publishing Group, vol. 4, No. 8, pp. 1128-1144.

(Continued)

*Primary Examiner* — Michael Rozanski
(74) *Attorney, Agent, or Firm* — Thomas | Horstemeyer, LLP

(57) ABSTRACT

A sonic window includes a body sized and configured to close an opening formed through the cranium, wherein at least a part of the body is made of a sonically transparent material through which ultrasonic waves can pass.

4 Claims, 9 Drawing Sheets

(56) References Cited

U.S. PATENT DOCUMENTS

| | | |
|---|---|---|
| 4,917,701 A | 4/1990 | Morgan |
| 4,936,852 A | 6/1990 | Kent et al. |
| 4,969,901 A | 11/1990 | Binder |
| 4,976,737 A | 12/1990 | Leake |
| 4,976,738 A | 12/1990 | Frey et al. |
| 4,978,355 A | 12/1990 | Frey et al. |
| 5,030,233 A | 7/1991 | Ducheyne |
| 5,139,497 A | 8/1992 | Tilghman et al. |
| 5,201,737 A | 4/1993 | Leibinger et al. |
| 5,218,975 A | 6/1993 | Prostkoff |
| 5,250,048 A | 10/1993 | Gundolf |
| 5,275,165 A | 1/1994 | Ettinger et al. |
| 5,282,861 A | 2/1994 | Kaplan |
| 5,290,315 A | 3/1994 | DeCarlo, Jr. |
| 5,346,492 A | 9/1994 | Morgan |
| 5,372,598 A | 12/1994 | Luhr et al. |
| 5,380,328 A | 1/1995 | Morgan |
| 5,383,931 A | 1/1995 | Hehli et al. |
| 5,397,361 A | 3/1995 | Clark |
| 5,421,831 A | 6/1995 | Giampapa |
| 5,433,996 A | 7/1995 | Kranzler et al. |
| 5,443,512 A | 8/1995 | Parr et al. |
| 5,443,519 A | 8/1995 | Averill et al. |
| 5,445,650 A | 8/1995 | Nealis |
| 5,456,723 A | 10/1995 | Steinemann et al. |
| 5,468,242 A | 11/1995 | Reisberg |
| 5,489,305 A | 2/1996 | Morgan |
| 5,496,371 A | 3/1996 | Eppley et al. |
| 5,496,372 A | 3/1996 | Hamamoto et al. |
| 5,545,226 A | 8/1996 | Wingo et al. |
| 5,554,194 A | 9/1996 | Sanders |
| 5,578,086 A | 11/1996 | Prescott |
| 5,669,909 A | 9/1997 | Zdeblick et al. |
| 5,690,631 A | 11/1997 | Duncan et al. |
| 5,728,157 A | 3/1998 | Prescott |
| 5,743,913 A | 4/1998 | Wellisz |
| 5,755,809 A | 5/1998 | Cohen et al. |
| 5,766,176 A | 6/1998 | Duncan |
| 5,769,637 A | 6/1998 | Morgan |
| 5,814,048 A | 9/1998 | Morgan |
| 5,824,088 A | 10/1998 | Kirsch |
| 5,863,297 A | 1/1999 | Walter et al. |
| 5,876,447 A | 3/1999 | Arnett |
| 5,980,540 A | 11/1999 | Bruce |
| 5,989,427 A | 11/1999 | Ellard et al. |
| 5,989,472 A | 11/1999 | Ashby et al. |
| 6,008,430 A | 12/1999 | White |
| 6,010,336 A | 1/2000 | Shimotoso et al. |
| 6,031,148 A | 2/2000 | Hayes et al. |
| 6,065,197 A | 5/2000 | Iseki et al. |
| 6,071,291 A | 6/2000 | Forst et al. |
| 6,087,553 A | 7/2000 | Cohen et al. |
| 6,093,188 A | 7/2000 | Murray |
| 6,120,539 A | 9/2000 | Eldridge et al. |
| 6,129,728 A | 10/2000 | Schumacher et al. |
| 6,143,036 A | 11/2000 | Comfort |
| 6,187,041 B1 | 2/2001 | Garonzik |
| 6,221,075 B1 | 4/2001 | Tormala et al. |
| 6,238,214 B1 | 5/2001 | Robinson |
| 6,267,772 B1 | 7/2001 | Mulhauser et al. |
| 6,270,530 B1 | 8/2001 | Eldridge et al. |
| 6,315,798 B1 | 11/2001 | Ashby et al. |
| 6,325,803 B1 | 12/2001 | Schumacher et al. |
| 6,350,284 B1 | 2/2002 | Tormala et al. |
| 6,391,059 B1 | 5/2002 | Lemperle et al. |
| 6,394,807 B2 | 5/2002 | Robinson |
| 6,475,094 B1 | 11/2002 | Bruns et al. |
| 6,524,345 B1 | 2/2003 | Valimaa et al. |
| 6,530,953 B2 | 3/2003 | Garonzik |
| 6,620,332 B2 | 9/2003 | Amrich |
| 6,645,250 B2 | 11/2003 | Schulter |
| 6,652,585 B2 | 11/2003 | Lange |
| 6,692,497 B1 | 2/2004 | Tormala et al. |
| 6,692,498 B1 | 2/2004 | Niiranen et al. |
| 6,827,743 B2 | 12/2004 | Eisermann et al. |
| 6,852,128 B2 | 2/2005 | Lange |
| 6,852,330 B2 | 2/2005 | Bowman et al. |
| 7,041,138 B2 | 5/2006 | Lange |
| 7,050,877 B2 | 5/2006 | Iseki et al. |
| 7,066,962 B2 | 6/2006 | Swords |
| 7,113,841 B2 | 9/2006 | Abe et al. |
| 7,208,222 B2 | 4/2007 | Rolfe et al. |
| 7,326,249 B2 | 2/2008 | Lange |
| 7,341,601 B2 | 3/2008 | Eisermann et al. |
| 7,614,258 B2 | 11/2009 | Cherok et al. |
| 7,655,047 B2 | 2/2010 | Swords |
| 7,662,155 B2 | 2/2010 | Metzger et al. |
| 8,298,292 B2 | 10/2012 | Swords et al. |
| 2001/0012607 A1 | 8/2001 | Robinson |
| 2002/0022883 A1 | 2/2002 | Burg |
| 2002/0050463 A1 | 5/2002 | McDowell |
| 2002/0120348 A1 | 8/2002 | Melican et al. |
| 2002/0123750 A1 | 9/2002 | Eisermann et al. |
| 2003/0208205 A1 | 11/2003 | Gambale |
| 2003/0220696 A1 | 11/2003 | Levine et al. |
| 2004/0019389 A1 | 1/2004 | Swords |
| 2004/0054372 A1 | 3/2004 | Corden et al. |
| 2004/0059356 A1 | 3/2004 | Gingras |
| 2004/0059422 A1 | 3/2004 | Koschatzky et al. |
| 2004/0267349 A1 | 12/2004 | Richter |
| 2005/0008660 A1* | 1/2005 | Kipke et al. .................. 424/400 |
| 2005/0043733 A1 | 2/2005 | Eisermann et al. |
| 2005/0146070 A1 | 7/2005 | Muratoglu et al. |
| 2005/0192675 A1 | 9/2005 | Robinson |
| 2005/0208095 A1 | 9/2005 | Hunter et al. |
| 2005/0288790 A1 | 12/2005 | Swords |
| 2006/0116682 A1 | 6/2006 | Longo |
| 2006/0217813 A1 | 9/2006 | Posnick et al. |
| 2006/0224242 A1 | 10/2006 | Swords et al. |
| 2007/0038100 A1 | 2/2007 | Nita |
| 2007/0156146 A1 | 7/2007 | Metzger et al. |
| 2008/0275402 A1 | 11/2008 | Schnell |
| 2009/0138067 A1 | 5/2009 | Pinchuk et al. |
| 2009/0216338 A1 | 8/2009 | Gingras et al. |
| 2010/0023130 A1 | 1/2010 | Henry et al. |
| 2010/0076555 A1 | 3/2010 | Marten et al. |
| 2013/0345599 A1 | 12/2013 | Lin et al. |

OTHER PUBLICATIONS

Sakaguchi, et al., "Influence of a Skull Cranial Window on the measurement of Haemoglobin Concentration in Cortical Tissue by Multi-Spectral Imaging Analysis", Optical Review, vol. 16, No. 2, pp. 74-80.

Fuller et al., "Real-Time Imaging with the Sonic Window: A Pocket-Sized, C-Scan, Medical Ultrasound Device," 2009 IEEE International Ultrasonics Symposium Proceedings, p. 196-199, 2009.

Tobias, et al., "An Ultrasound Window to Perform Scanned, Focused Ultrasound Hyperthermias Treatements of Brain Tumors", Med. Phys 14 (2), Mar./Apr. 1987, pp. 228-234.

Looi, et al. "Porcine Pilot Study of MRI-guided HIFU Treatement for Neonatal Intraventricular Hemorrhage (IVH)", 12 International Symposium on Therapeutic Ultrasound, AIP Conf. Proc. 1503, 233-238 (2012).

Damestani, et al., "Transparent Nanocrystalline yttria-stabilized-zirconia calvarium prosthesis", Nanomedicine: Nanotechnology, Biology, and Medicine, 1135-1138, (2013).

* cited by examiner

IMPLANTABLE SONIC WINDOWS

CROSS-REFERENCE TO RELATED APPLICATION(S)

This application claims priority to U.S. Provisional Application Ser. No. 61/818,724, filed May 2, 2013, which is hereby incorporated by reference herein in its entirety.

BACKGROUND

Brain imaging is typically used for management of many neurosurgical conditions. Most often, computed tomography (CT) and/or magnetic resonance imaging (MRI) are the modalities used to image the brain in such cases. While such modalities can be effective, neither is ideal. CT scanning is currently falling out of favor because of the risk of inducing neoplasia, while MRI is unattractive because of its high cost and the need for patient sedation.

In view of the above discussion, it can be appreciated that it would be desirable to have an alternative way to image the brain.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an alternative way to image the brain. As disclosed herein, the brain can be imaged by forming an opening in the cranium and performing ultrasound imaging through the opening. In some embodiments, the opening in the cranium can be closed with an implantable sonic window that provides protection to the brain and prevents deformation of the brain due to pressure changes but that also permits ultrasonic waves to freely pass into and out from the brain. In some embodiments, the sonic window is made of a sonically translucent polymeric material.

In the following disclosure, various specific embodiments are described. It is to be understood that those embodiments are example implementations of the disclosed inventions and that alternative embodiments are possible. All such embodiments are intended to fall within the scope of this disclosure.

Figure 1A:
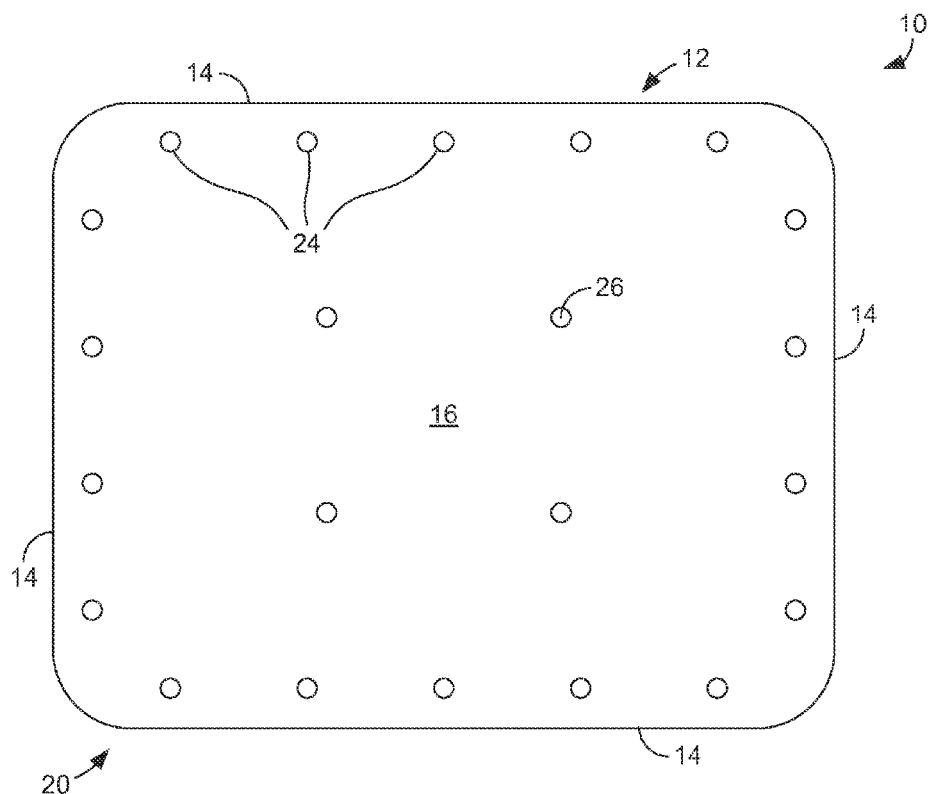
FIG. 1A is a top view of a first embodiment of an implantable sonic window.
Figure 1B:
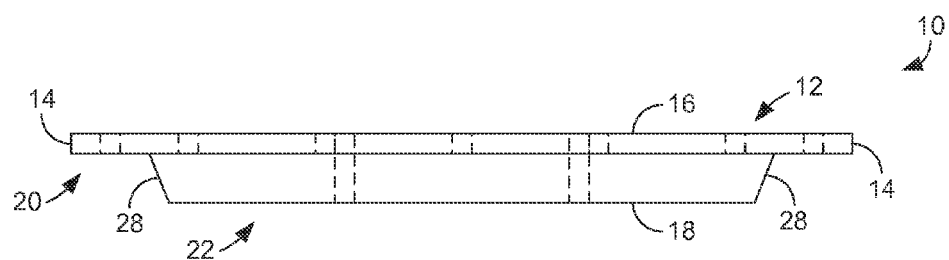
FIG. 1B is a side view of the sonic window of FIG. 1A.

FIGS. 1A and 1B illustrate a first embodiment of a sonic window 10 that can be used to close an opening formed in the cranium for purposes of ultrasound imaging of the brain. As shown in the figures, the window 10 comprises a generally planar body 12 that is unitarily formed from a single piece of material. In some embodiments, the material is a strong but porous sonically translucent material through which ultrasonic waves can pass for purposes of imaging the brain. By way of example, the material is a polymeric material, such as polyethylene, polystyrene, acrylic, or poly(methyl methacrylate) (PMMA). In some embodiments, the polymeric material has a porosity of approximately 20 to 500 µm. While the body 12 has been described as being "planar," it is noted that, in at least some embodiments, the body can be curved to match the contours of the cranium to which it is to be applied. Such curvature can be provided during manufacturing of the sonic window 10 or can be achieved by the user (e.g., surgeon) prior to implantation of the sonic window. In the latter case, the body 12 can be curved by first heating it to a temperature at which its material is malleable.

In the illustrated embodiment, the body 12 is generally rectangular such that it includes four corners and four outer edges 14. In such a case, the body 12 can have length and width dimensions of approximately 2 to 3 cm. Other dimensions are possible, however, and, in general, the dimensions will correspond to the size of the opening that has been formed through the cranium. While the body 12 is shown as being rectangular in FIGS. 1A and 1B, it is noted that the body can have substantially any shape. For instance, FIGS. 3A and 3B, which are described below, show a sonic window having a circular body.

As is further shown in FIGS. 1A and 1B, the body 12 includes an outer surface 16 and an inner surface 18. As indicted in FIG. 18, the body 12 defines a peripheral portion 20, which is applied to the outer surface of the cranium, and a central portion 22, which fits within the opening formed through the cranium. The peripheral portion 20 can be approximately 1 to 2 mm thick so that the window 10 will only minimally extend upward from the outer surface of the cranium while the central portion 22 can be approximately 1 to 8 mm thick. As is further shown in FIG. 1B, outer edges 28 of the central portion 22 can be angled such that the central portion gradually tapers from the peripheral 20 portion to facilitate insertion of the central portion into the cranium opening.

With reference back to FIG. 1A, peripheral mounting holes 24 are formed through the peripheral portion 20 of the body 12. In the illustrated embodiment, 4 to 5 holes 24 are formed along each side of the body 12, although each side can comprise a larger or smaller number of holes. The holes 24 are adapted to receive fastening elements that can pass through the body 12 and into the bone of the cranium. By way of example, the fastening elements can comprise screws, bone anchors, sutures, or wires. In some embodiments, the holes are approximately 1 mm in diameter.

The body 12 further includes central mounting holes 26 formed in the central portion 22 of the body that are adapted to receive fastening elements that can pass through the body and anchor in the dura overlying the brain. In such a case, the dura can be supported by the sonic window 10 to prevent fluid from collecting between the window and the dura. By way of example, the fastening elements can comprise soft-tissue anchors, sutures, or wires.

Figure 2A:
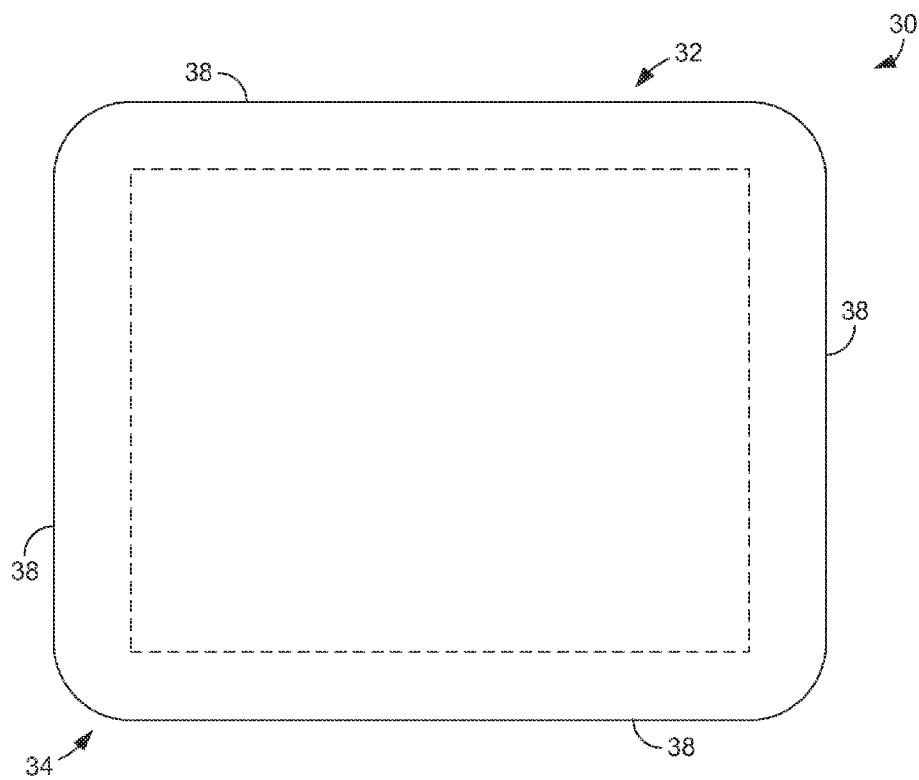
FIG. 2A is a top view of a second embodiment of an implantable sonic window.
Figure 2B:
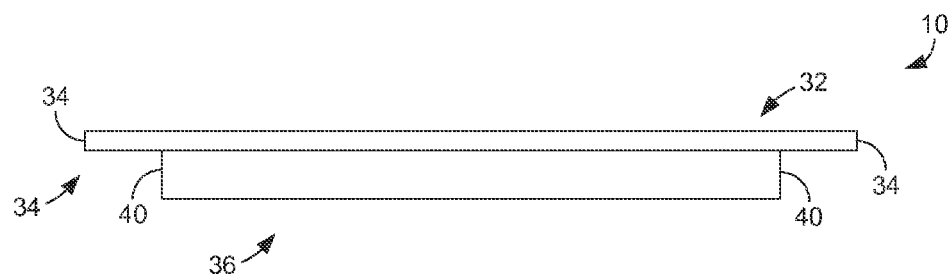
FIG. 2B is a side view of the sonic window of FIG. 2A.

FIGS. 2A and 2B illustrate a second embodiment of a sonic window 30. The sonic window 30 is similar in several ways to the sonic window 10 shown in FIGS. 1A and 1B. Accordingly, the sonic window 30 generally comprises a planar body 32 that is made of a sonically translucent polymeric material and that defines a peripheral portion 34 and a central portion 36. The peripheral portion 34 comprises multiple edges 38 and the central portion 36 comprises multiple edges 40. Unlike the sonic window 10, however, the sonic window 30 does not include mounting holes. Instead the sonic window 30 is adapted to attach to the cranium using adhesive or a press fit. In the former case, adhesive, such as cyanoacrylate, can be applied to the inner surface of the peripheral portion 34 and/or the outer surface of the cranium and the sonic window 30 can be placed over the opening in the cranium. Once the adhesive has cured, the sonic window 30 will be secured to the cranium. In the latter case, the central portion 36 of the body 32 can have a similar shape and dimension as the cranium opening such that, when the central portion is pressed into the cranium opening, the sonic window 30 will be held in place by friction. As shown in FIG. 2B, the edges 40 of the central portion 36 can be generally perpendicular to the inner surface of the peripheral portion 34 (and therefore the outer surface of the cranium) to facilitate such a fit. Alternatively, the peripheral portion 34 can be melted with locally applied heat to fuse it to the margins of the craniotomy defect. Bone staples can also be used to further secure the sonic window 30 in place.

Figure 3A:
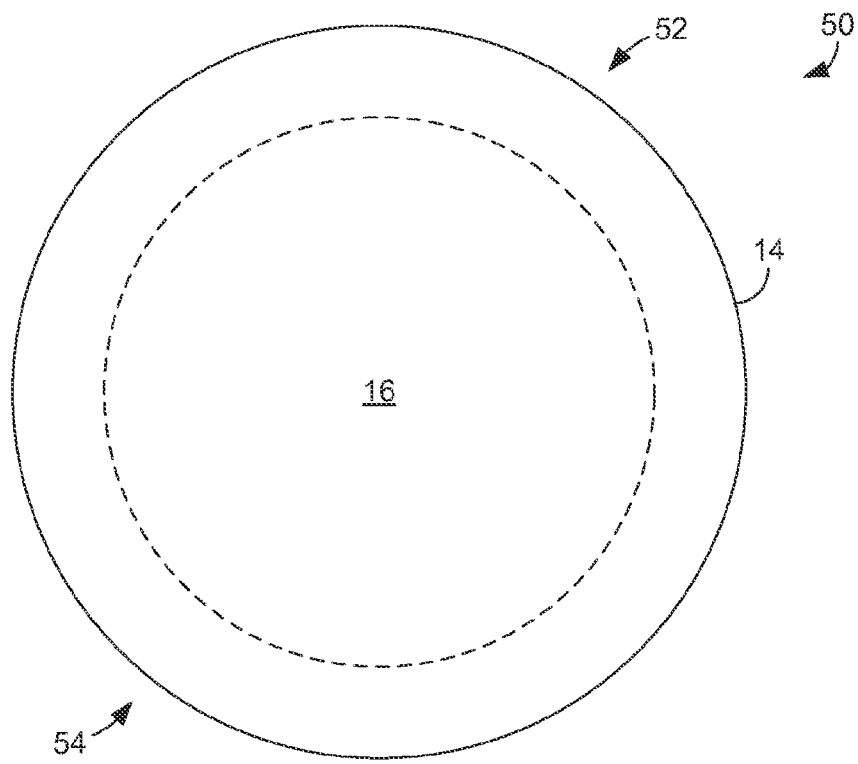
FIG. 3A is a top view of a third embodiment of an implantable sonic window.
Figure 3B:
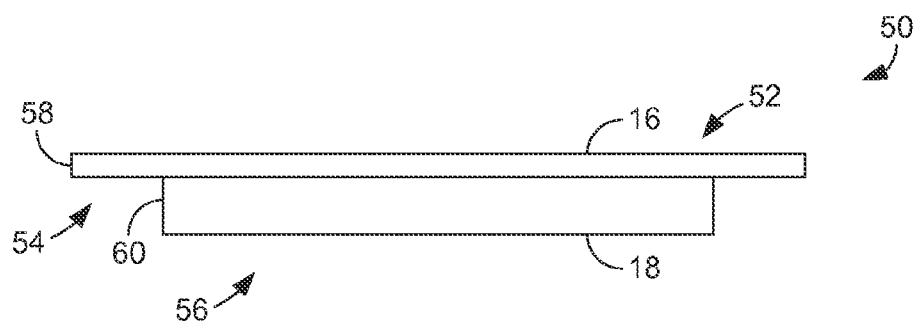
FIG. 3B is a side view of the sonic window of FIG. 3A.

FIGS. 3A and 3B illustrate a third embodiment of a sonic window 50. The sonic window 50 is similar in several ways to the sonic window 30 shown in FIGS. 2A and 2B. Accordingly, the sonic window 50 generally comprises a planar body 52 that is made of a sonically translucent polymeric material and that defines a peripheral portion 54 and a central portion 56. Unlike the sonic window 30, however, the sonic window 50 is circular. Therefore, the peripheral portion 54 comprises a circular outer edge 58 and the central portion 56 comprises a circular outer edge 60. In some embodiments, the sonic window 50 can be used as a burr hole cover through which ultrasonic waves can pass. In such an application, the central portion 56 can have a diameter of approximately 1 to 2 cm.

Figure 4A:
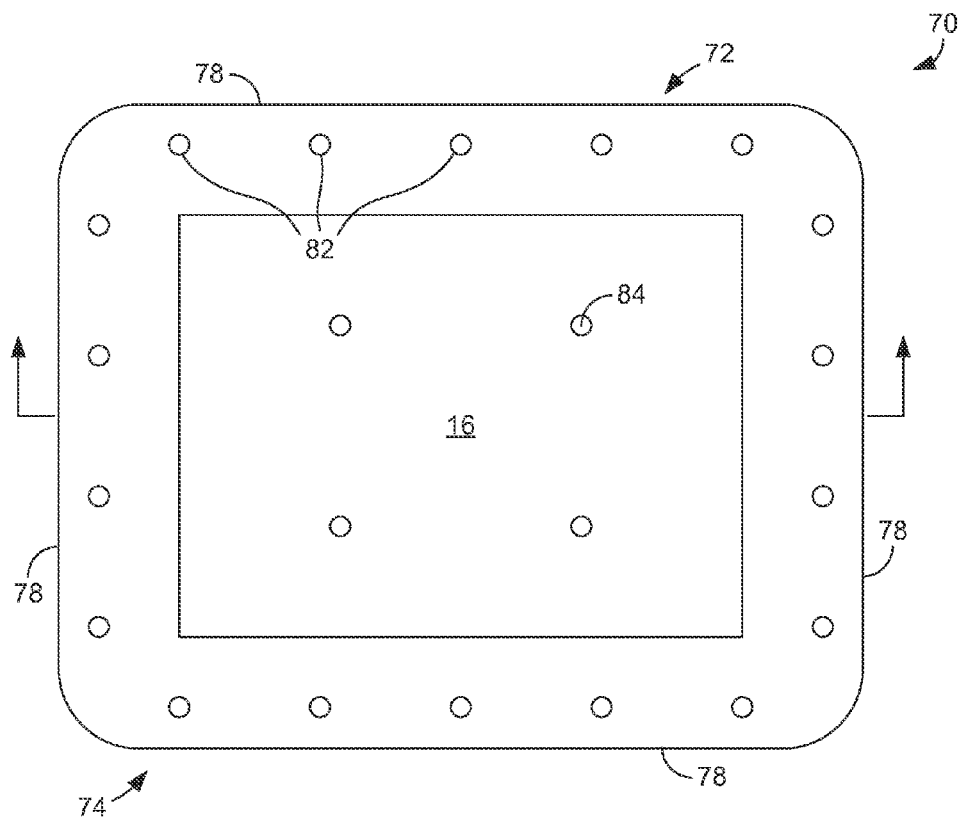
FIG. 4A is a top view of a fourth embodiment of an implantable sonic window.
Figure 4B:
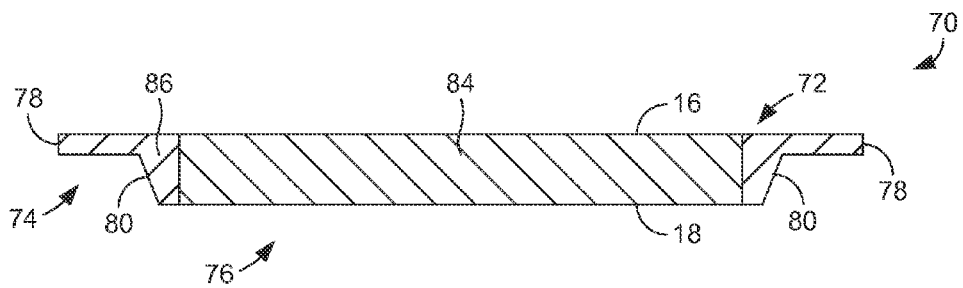
FIG. 4B is a cross-sectional side view of the sonic window of FIG. 4A.

FIGS. 4A and 4B illustrate a fourth embodiment of a sonic window 70. The sonic window 70 is similar in several ways to the sonic window 10 shown in FIGS. 1A and 1B. Accordingly, the sonic window 70 generally comprises a planar body 72 that defines a peripheral portion 74 and a central portion 76. The peripheral portion 74 comprises multiple edges 78 and the central portion 36 comprises multiple edges 80. In addition, mounting holes 82 are provided through the peripheral portion 74 and central mounting holes 84 are provided through the central portion 76. Unlike the sonic window 10, however, at least part of the central portion 76 is made of a lower-density, higher-porosity material 84 through which ultrasound waves can easily pass while the peripheral portion 74 is made of a high-density, lower-porosity material 86 through which ultrasound waves cannot easily pass but that is stronger than the higher-porosity material. In some embodiments, the material 84 of the central portion 76 is a polymeric material such polyethylene, polystyrene, acrylic, or PMMA while the material 86 of the peripheral portion 74 is made of silicone, polyoxymethylene (POM), high grade polytetrafluoroethylene (PTFE), or a biocompatible metal, such as titanium or stainless steel.

Figure 5A:
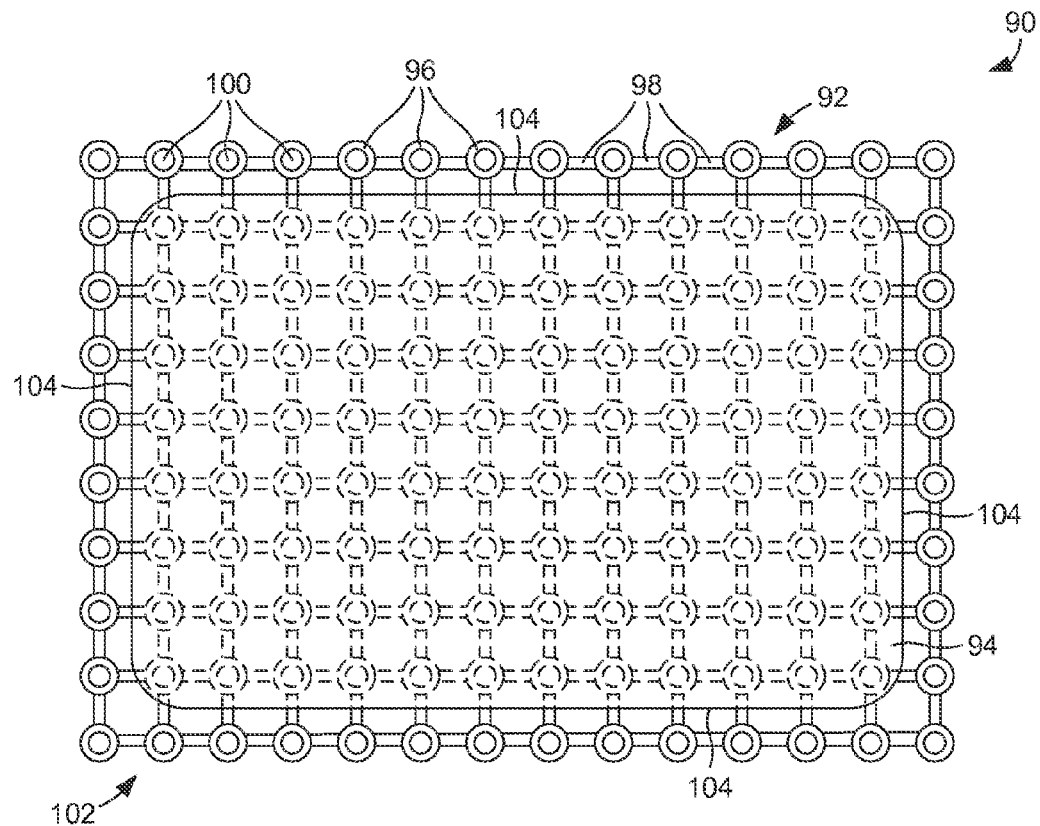
FIG. 5A is a top view of a fifth embodiment of an implantable sonic window.
Figure 5B:
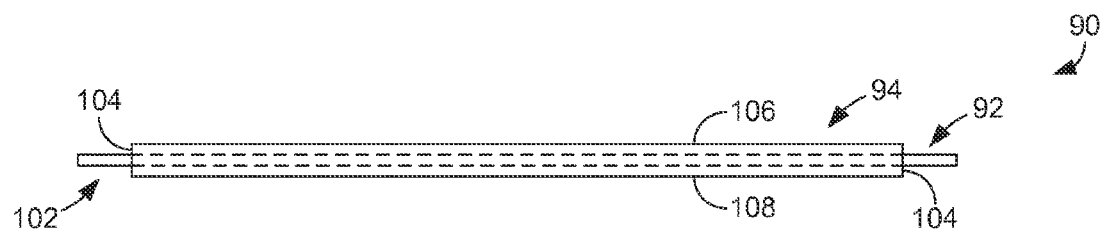
FIG. 5B is a side view of the sonic window of FIG. 5A.

In some embodiments, a sonic window can comprise a metal mesh that provides strength to and facilitates shaping of the sonic window. FIGS. 5A and 5B illustrate an example of such a sonic window 90. As indicated in these figures, the sonic window 90 generally comprises a mesh 92 that is partially encapsulated in a body 94 of sonically translucent material. In the illustrated embodiment, the mesh 92 comprises a matrix of circular elements 96 that are connected within the matrix by linear links 98. Each of the circular elements 96 includes a circular opening 100 through which a fastening element, such as a screw, bone anchor, suture, or wire, can pass. In some embodiments, the mesh 92 is made of titanium or a titanium alloy.

The body 94 can be made of a sonically translucent polymer material, such as polyethylene, polystyrene, acrylic, or PMMA. As is apparent in FIG. 5B, the body 94 can encapsulate a central portion of the mesh 92 (on all sides) but stop short of encapsulating the edges of the mesh, which form a peripheral portion 102 that can be used to secure the sonic window 90 in place on the cranium. Accordingly, the mesh 92 extends beyond the outer edges 104 of the body 94. With further reference to FIG. 5B, the body 94 further comprises an outer surface 106 and an inner surface 108 and can be approximately 0.5 to 1 mm thick. The mesh 92 can, for example, be encapsulated by the material of the body 94 using an injection molding process or by applying separate pieces of the body material to the outer and inner sides of the mesh and fusing the pieces together to form a monolithic body.

Although the material of the mesh 92 is not sonically translucent, the mesh is relatively course so that ultrasonic waves can pass through the mesh. In some embodiments, appropriate image-processing software can be used to attenuate any interference created by the mesh 92 so that a clean ultrasound image can be reconstructed.

Figure 6A:
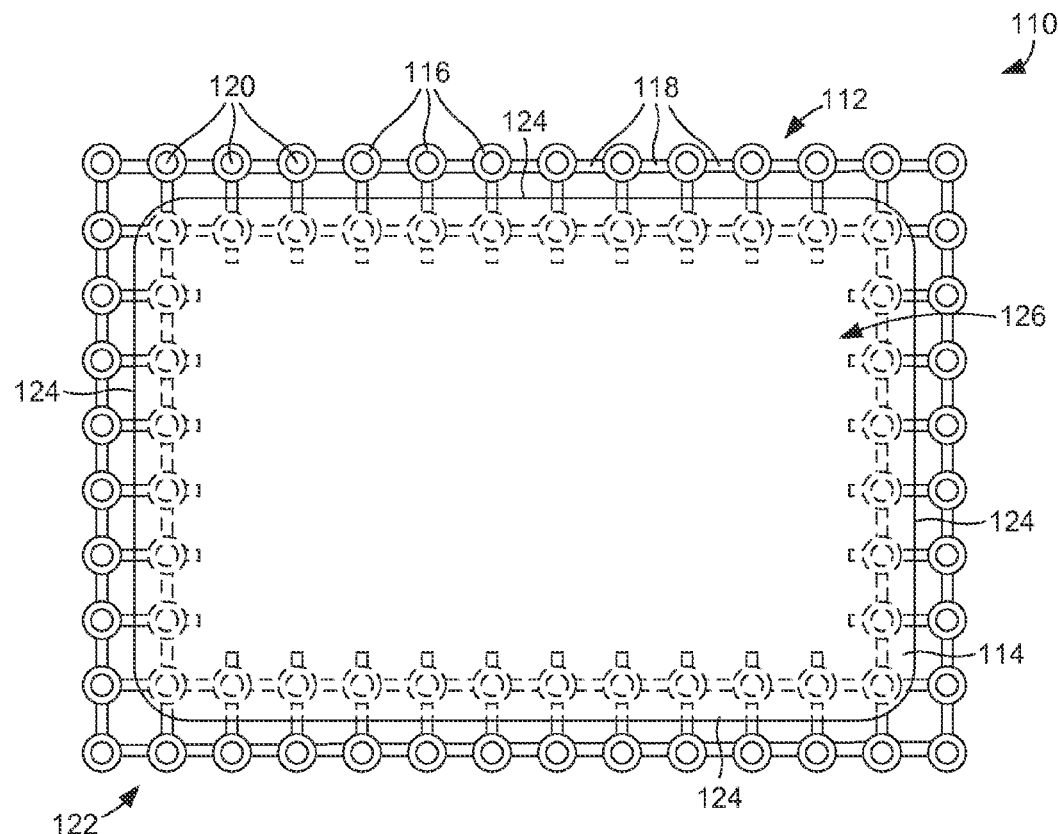
FIG. 6A is a top view of a sixth embodiment of an implantable sonic window.
Figure 6B:
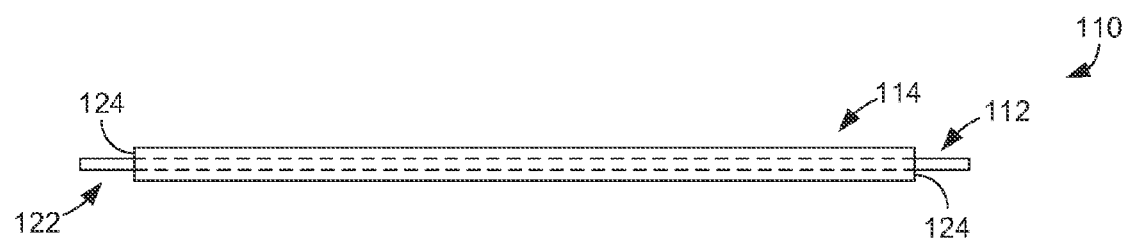
FIG. 6B is a side view of the sonic window of FIG. 6A.

FIGS. 6A and 6B illustrate a further embodiment of a sonic window 110. The sonic window 110 is similar in several ways to the sonic window 90 shown in FIGS. 5A and 5B. Accordingly, the sonic window 110 generally comprises a mesh 112 that is partially encapsulated in a body 114 of sonically translucent material. The mesh 112 comprises a matrix of circular elements 116 that are connected within the matrix by linear links 118. Each of the circular elements 116 includes a circular opening 120 through which a fastening element, such as a screw, bone anchor, suture, or wire, can pass. The body 114 encapsulates a central portion of the mesh 112 (on all sides) but stops short of encapsulating the edges of the mesh so as to form a peripheral portion 122 of mesh that extends beyond the outer edges 124 of the body 114. Unlike the sonic window 90, however, the mesh 112 has a central opening 126 (that is encapsulated within the body 114) that enables ultrasonic waves to pass unimpeded through the window 110.

Figure 7A:
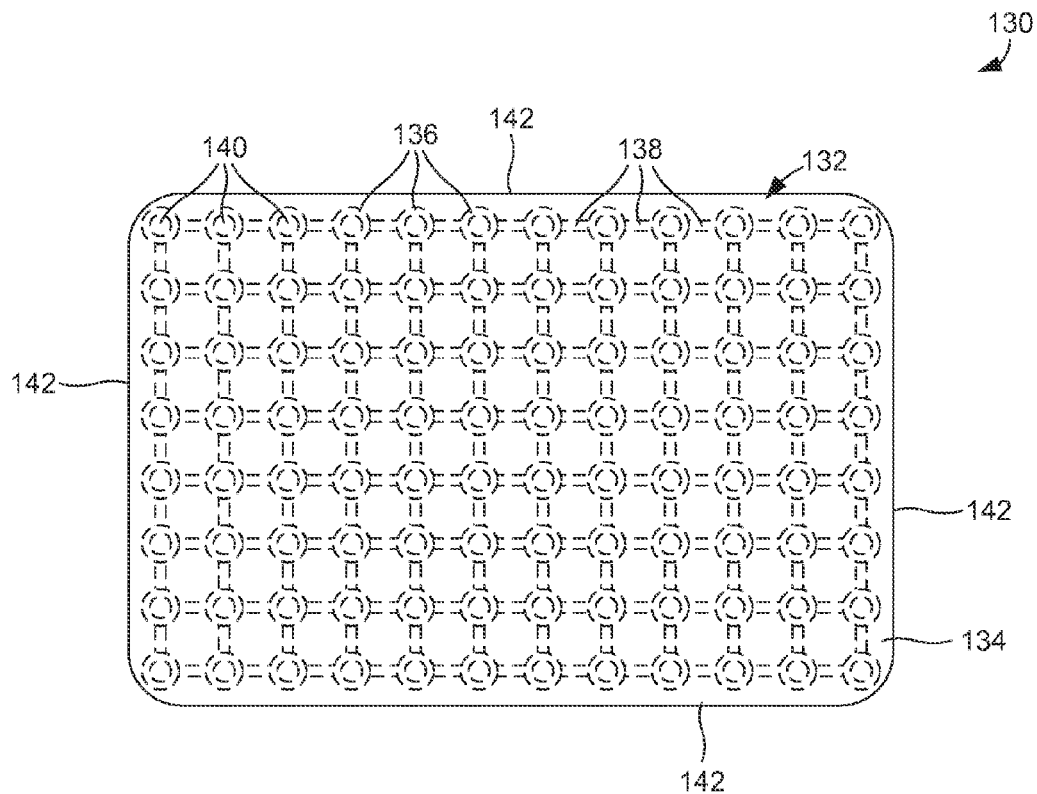
FIG. 7A is a top view of a seventh embodiment of an implantable sonic window.
Figure 7B:
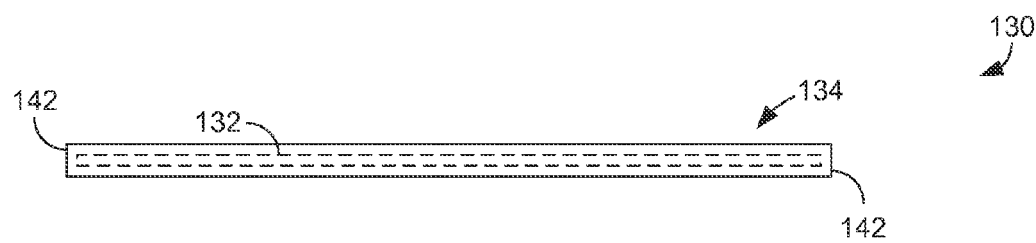
FIG. 7B is a side view of the sonic window of FIG. 7A.

FIGS. 7A and 7B illustrate another embodiment of a sonic window 130. The sonic window 130 is similar in several ways to the sonic window 90 shown in FIGS. 5A and 5B. Accordingly, the sonic window 130 generally comprises a mesh 132 that is encapsulated in a body 134 of sonically translucent material. The mesh 132 comprises a matrix of circular elements 136 that are connected within the matrix by linear links 138. Each of the circular elements 136 includes a circular opening 140 through which a fastening element, such as a screw, bone anchor, suture, or wire, can pass. Unlike the mesh 92 of the sonic window 90, the mesh 132 of the sonic window 130 is completely encapsulated within the body 134 such that no edges of the mesh extend beyond the edges 142 of the body.

Figure 8A:
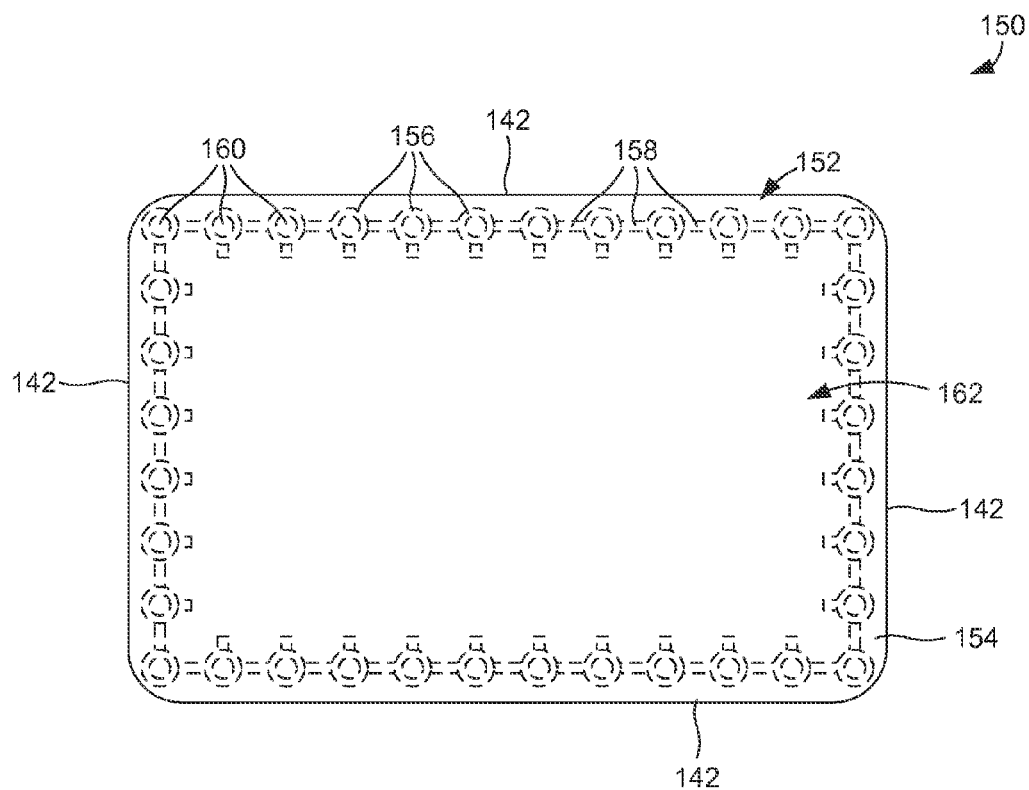
FIG. 8A is a top view of a eighth embodiment of an implantable sonic window.
Figure 8B:
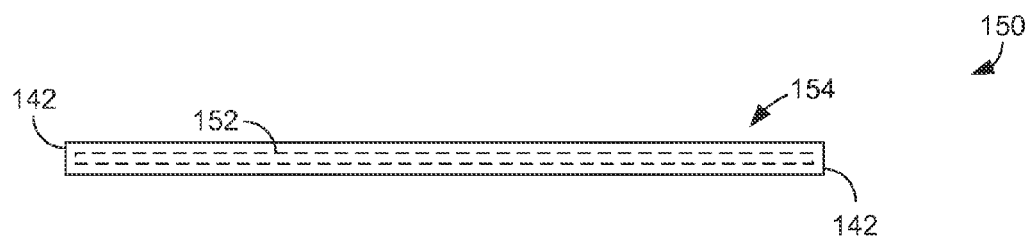
FIG. 8B is a side view of the sonic window of FIG. 8A.

FIGS. 8A and 8B illustrate another embodiment of a sonic window 150. The sonic window 150 is similar in several ways to the sonic window 130 shown in FIGS. 7A and 7B. Accordingly, the sonic window 150 generally comprises a metal mesh 152 that is wholly encapsulated in a body 154 of sonically translucent material. The mesh 152 comprises a matrix of circular elements 156 that are connected within the matrix by linear links 158. Each of the circular elements 136 includes a circular opening 160 through which a fastening element, such as a screw, bone anchor, suture, or wire, can pass. Unlike the mesh 132 of the sonic window 130, the mesh 152 of the sonic window 150 has a central opening 162 that enables ultrasonic waves to pass unimpeded through the sonic window 150.

Figure 9:
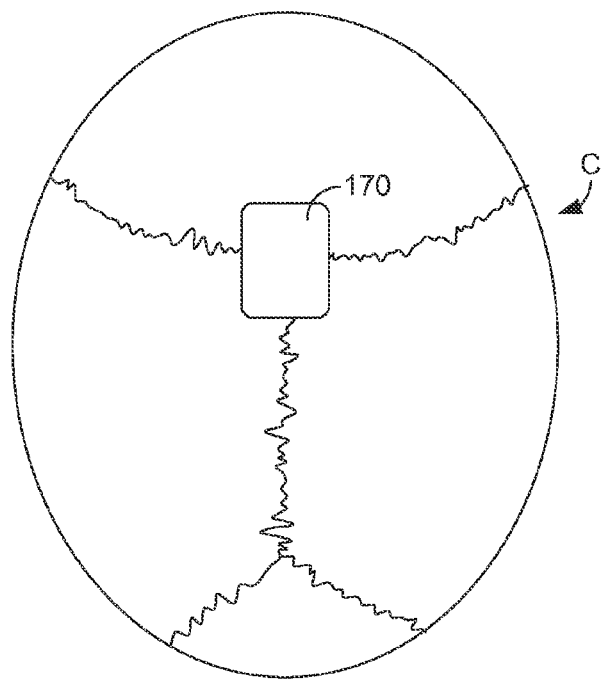
FIG. 9 is a top view of a sonic window implanted within a patient.
Figure 10:
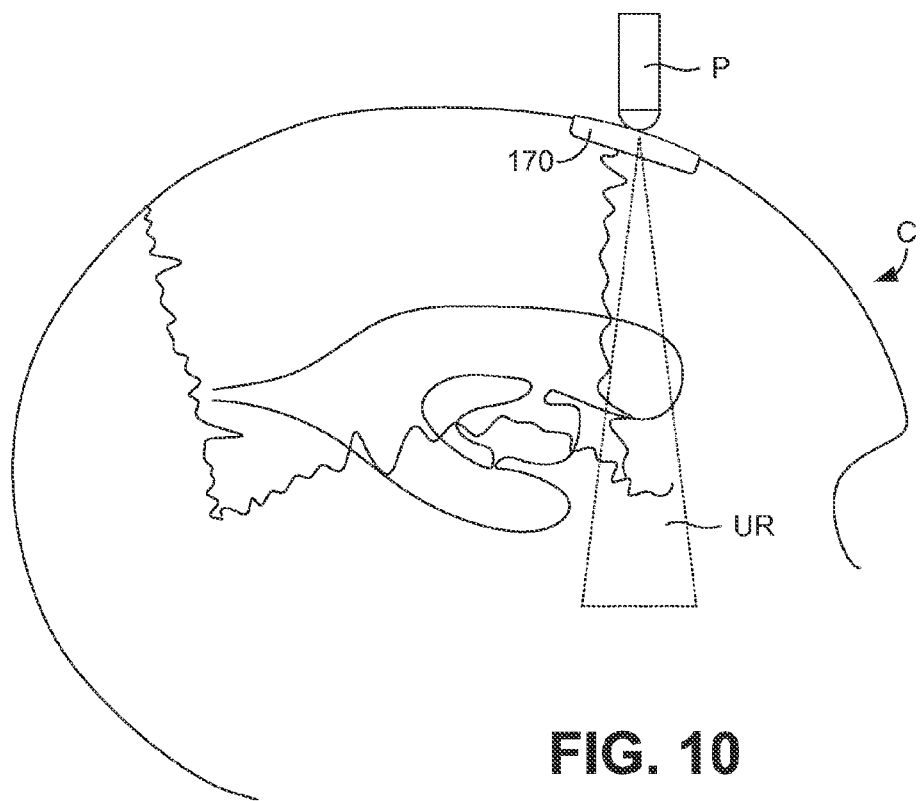
FIG. 10 is a side view of a patient with an implanted sonic window and illustrates ultrasound imaging through the sonic window.

FIGS. 9 and 10 illustrate implantation of an example sonic window 170 to the cranium C of a patient. As shown in FIG. 9, the sonic window 170 can be implanted at the bregma. In such a case, an opening would be formed through the cranium at the bregma and the sonic window 170 would be secured to the cranium C in a manner in which it covers the opening. The scalp can then be closed over the sonic window 170. While the bregma is a convenient location for the sonic window 170, it is noted that the sonic window 170 can be implanted at substantially any location on the cranium.

As mentioned above, the sonic windows can be used in a diagnostic manner to image the tissues of the brain. FIG. 10 illustrates an example of this. As shown in that figure, the tip of an ultrasound probe P can be positioned at the sonic window 170 after it has been implanted (and after the scalp has been closed) to transmit ultrasonic radiation UR through the window and into the brain. Although images obtained from the ultrasound imaging may provide enough information on their own, it is noted that other imaging modalities can be used to supplement that information. For example, if desired, CT scanning and/or MRI imaging can be used in conjunction with the ultrasound imaging to obtain a more complete picture of what is happening within the patient's brain.

It is further noted that the sonic windows can be used in a therapeutic manner. For example, focused ultrasound waves can be transmitted through the sonic window 170 to provide deep tissue heating and/or ablation of target tissue (e.g., a tumor). As a further example, continuous ultrasonic imaging could be performed through the sonic window to facilitate of a positioning of a catheter within the brain tissue. Furthermore, continuous ultrasonic imaging can be performed to observe tissue ablation performed using another means, such as electrosurgery, mechanical compression, extraction, laser, or ultrasonic disruption and aspiration. Additionally, ultrasound thermometry (i.e., measuring tissue temperature by using ultrasonic imaging algorithms) could be used to obtain continuous monitoring of a moving front of thermal change as delivered by another heating means, such as laser energy via a fiberoptic catheter or sound energy through focused ultrasound. It is also possible to deliver focused ultrasound across the sonic window toward a target while monitoring diagnostically or thermographically aside the energy means or even integrated into the energy means.

It is also noted that a piezoelectric transducer can be positioned outside of the head overlying the sonic window. The transducer can be directed at a subjacent tissue while monitoring with a diagnostic ultrasound probe. Such tissue sound actuation may have unique therapeutic effects. These effects can alter permeability to a chemotherapeutic drug across the blood brain barrier. Alternatively, they can activate or suppress neural function in a scheme of neuromodulation. Examples include the treatment of depression and other mood disorders and facilitating rehabilitation post brain injury in stroke.

It is further noted that a sonic window can be made of a material that is substantially more transmissive of particular light frequencies than the cranium. For example, near infrared and visible red light density and scattering could be optimized into a tissue for purposes of monitoring of pulsatile blood flow and oxygen saturation. Alternatively, the therapeutic effect of such light upon tissue reserves against oxidative stress or upregulating mitochondrial energy production could be enhanced through such a sonic window.

The invention claimed is:

1. A diagnostic or therapeutic ultrasonic method comprising:
    forming an opening through the cranium;
    closing the opening with a sonic window made of a sonically translucent material through which ultrasonic waves can pass;
    securing the sonic window to the cranium using a press fit or by fusing it to the cranium such that no fasteners or adhesives are used;
    closing the scalp over the sonic window; and
    transmitting ultrasonic waves into the brain through the sonic window.

2. The method of claim 1, further comprising imaging the brain using ultrasonic waves reflected from the brain.

3. The method of claim 1, wherein the ultrasonic waves are focused waves and further comprising ablating target tissue within the brain with the ultrasonic waves.

4. The method of claim 1, further comprising measuring tissue temperature with the ultrasonic waves.

* * * * *